United States Patent [19]

Cofone et al.

[11] Patent Number: 5,341,815
[45] Date of Patent: Aug. 30, 1994

[54] ENDOSCOPIC SURGICAL POUCH

[75] Inventors: Mark A. Cofone, Glen Gardner; Lee P. Bendel, Lebanon, both of N.J.

[73] Assignee: Ethicon, Inc., Somerville, N.J.

[21] Appl. No.: 37,055

[22] Filed: Mar. 25, 1993

[51] Int. Cl.⁵ ............................................. A61B 10/00
[52] U.S. Cl. ...................... 128/749; 604/281; 128/DIG. 24; 600/37
[58] Field of Search .............. 604/327, 328, 281; 606/114, 139, 151; 128/749, DIG. 24; 600/37

[56] References Cited

U.S. PATENT DOCUMENTS

| | | | |
|---|---|---|---|
| 5,037,379 | 8/1991 | Clayman et al. | 600/37 |
| 5,143,082 | 9/1992 | Kindberg et al. | 128/749 |
| 5,147,371 | 9/1992 | Washington et al. | 606/127 |
| 5,171,233 | 12/1992 | Amplatz et al. | 604/281 |
| 5,190,555 | 3/1993 | Wetter et al. | 606/114 |
| 5,215,521 | 6/1993 | Cochran et al. | 604/22 |
| 5,219,358 | 6/1993 | Bendel et al. | 606/222 |

Primary Examiner—John D. Yasko
Assistant Examiner—Connie Maglione
Attorney, Agent, or Firm—Emil Richard Skula

[57] ABSTRACT

A medical device for enclosing an internal body organ or tissue during surgery, especially endoscopic surgery. The device has a strand with loop and free end portions, the free end portion enclosed within a cannula. The loop has a cinch. The device has a surgical pouch with an opening or mouth. The pouch is mounted to the loop portion at the open end of the pouch. An optional frangible end of the cannula allows for pulling the free end portion proximally to reduce the diameter of the noose portion so as to close the open end of the surgical pouch. The surgical pouch has a shape memory effect metal insert so that the pouch automatically unfurls or unwinds in a patient's body cavity. The device may also have a shape memory effect metal loop which also automatically opens the mouth of the pouch in the patient's body.

39 Claims, 9 Drawing Sheets

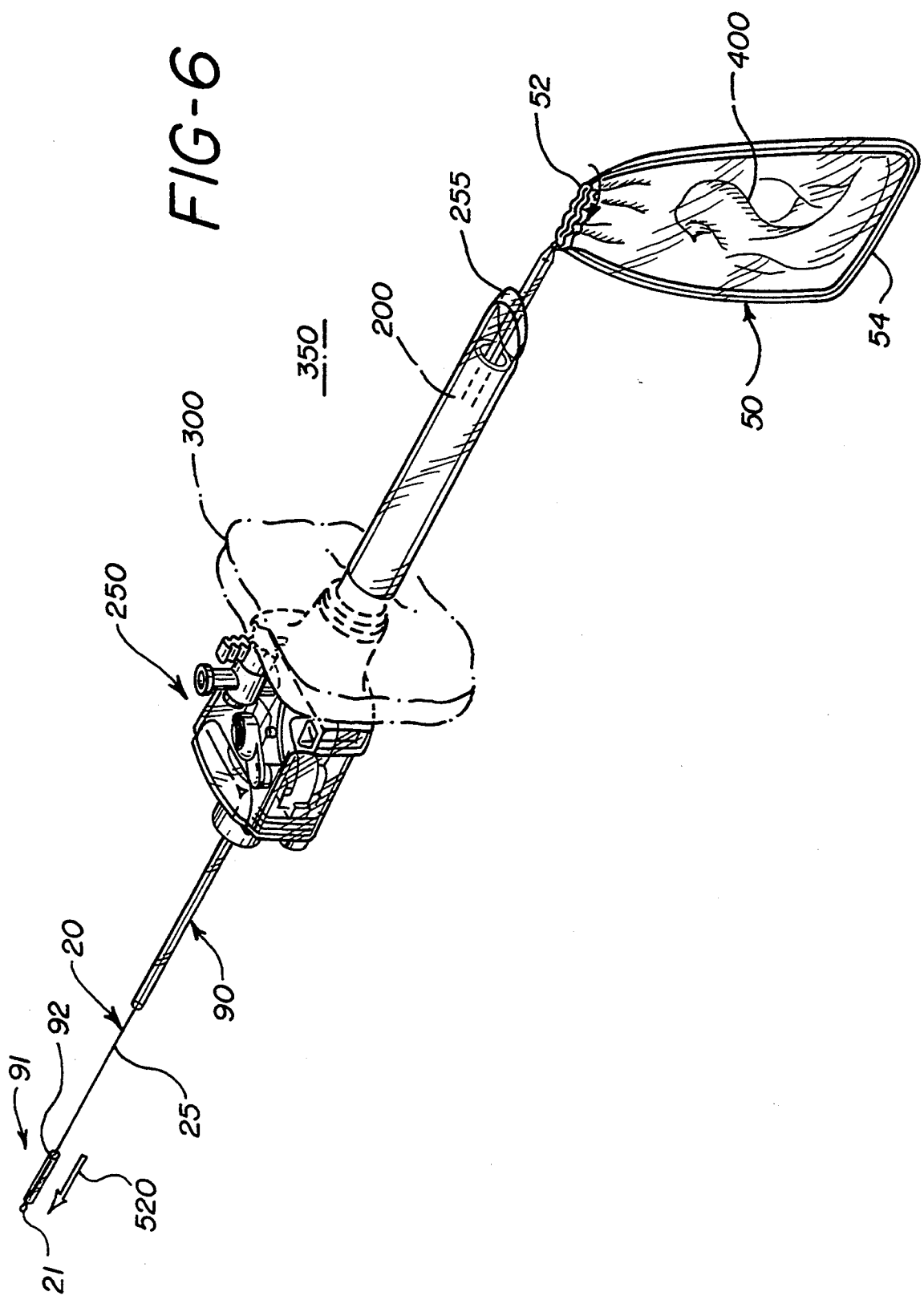

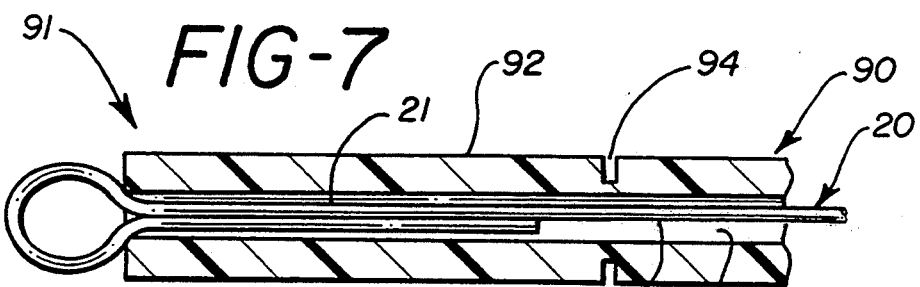
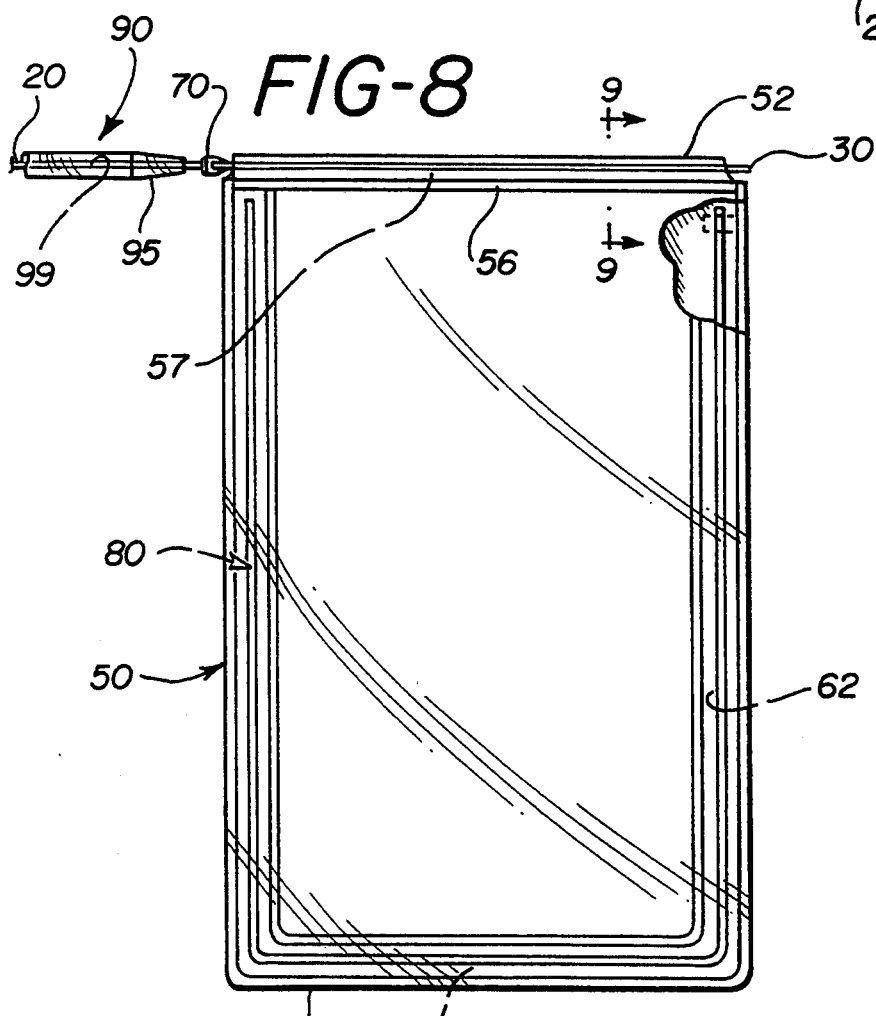
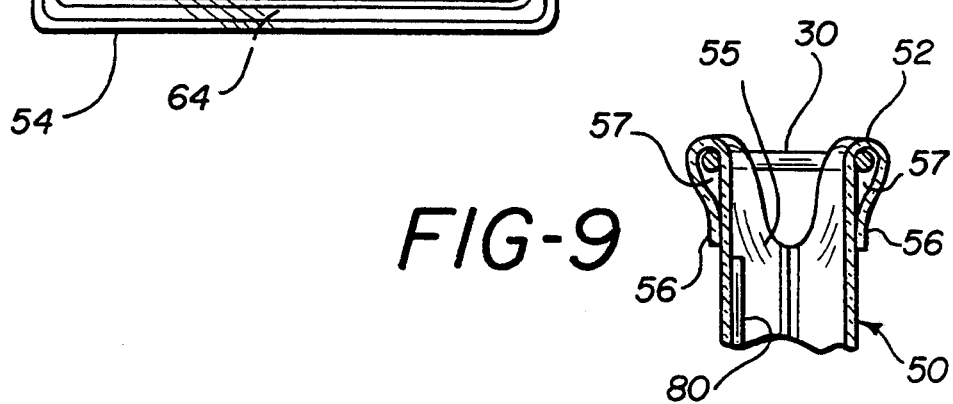

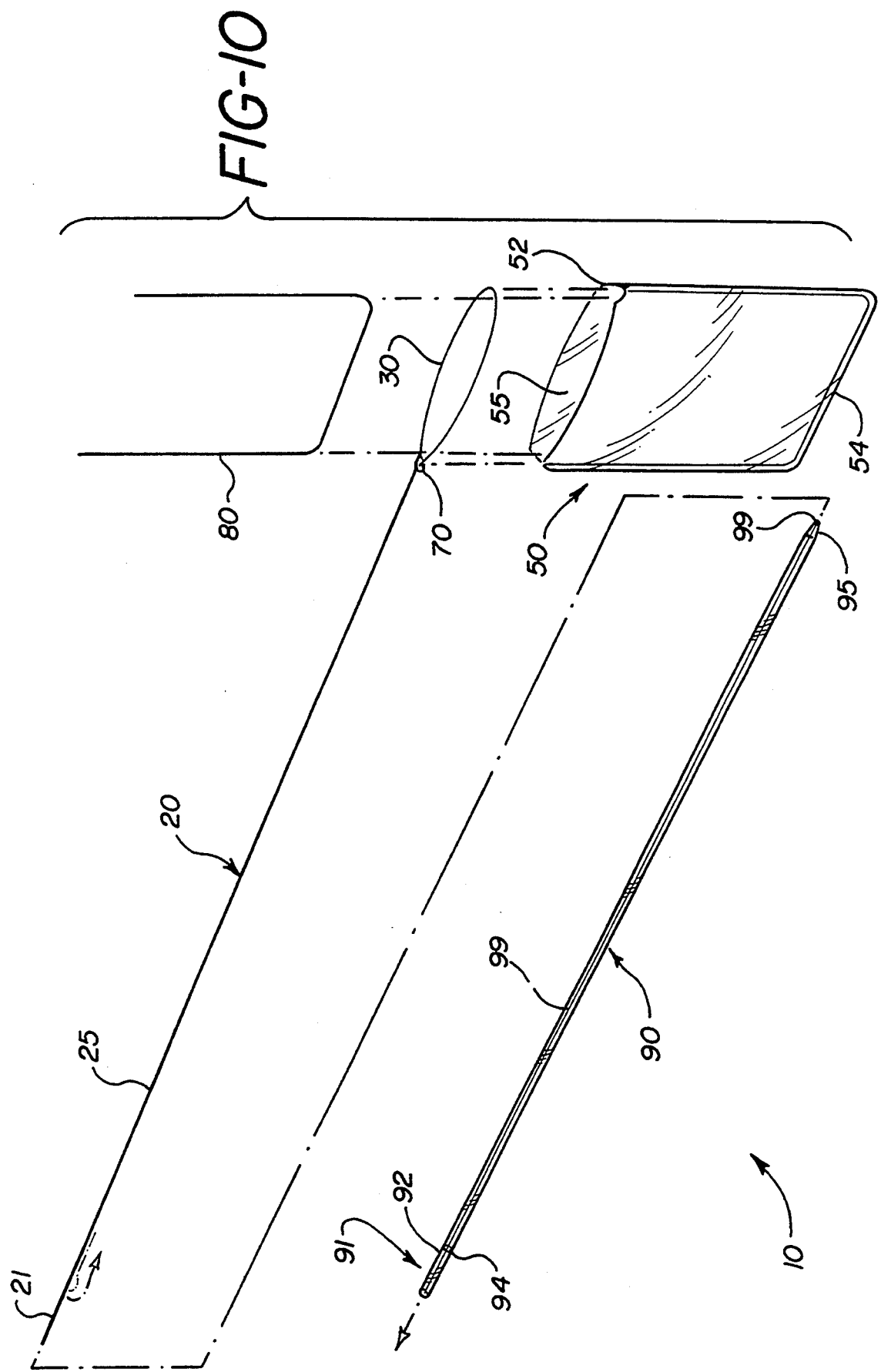

ENDOSCOPIC SURGICAL POUCH

TECHNICAL FIELD

The field of art to which this invention relates is surgical instrumentation, in particular endoscopic surgical instruments.

BACKGROUND OF THE INVENTION

The use of endoscopic surgical procedures has become increasingly accepted throughout the surgical community. There are many advantages associated with the use of endoscopic surgical techniques including improved post-operative recuperation, decreased avenues for infection, and decreased post-operative hospital stays. The term endoscopic as used herein is meant to encompass all minimally invasive surgical techniques utilizing a scope including endoscopic, laparoscopic, thoracoscopic and arthroscopic.

In many endoscopic surgical techniques, it is necessary to enter a body cavity to obtain access to a target surgical site. This is conventionally done by using a conventional trocar. A trocar typically consists of a trocar obturator having a sharp piercing point and a trocar cannula. The trocar obturator is concentrically housed within the trocar cannula during insertion through the musculature and fascia surrounding the body cavity. The trocar obturator is then removed from the trocar cannula after the trocar has been maneuvered into the body cavity, leaving the trocar cannula as a pathway into the body cavity, e.g., the abdomen.

Numerous surgical instruments have been developed and adapted for endoscopic surgical techniques. For example, there are stapling apparatuses, suture and cannula assemblies, electrocautery devices, tissue manipulating devices, tissue cutting devices, tissue ligating devices, and the like. Frequently, it is necessary for the surgeon to manipulate or move internal organs such as the liver, the spleen, and the gall bladder in order to access the target surgical site. This is typically done with a variety of tissue manipulators which have been specially developed for this task.

In many surgical procedures, including those involved in endoscopic surgery, it is often necessary to remove tissue or damaged organs. This is especially challenging during endoscopic surgery because of the small openings (i.e., trocar cannulas) through which such tissue or organs must be removed. Under these circumstances, it may be necessary to fragment, or morcellate, the tissue so that it can be readily removed through the small endoscopic openings.

In response to the need to morcellate and remove tissue during endoscopic surgery, tissue morcellators have been developed to aid the surgeon. The tissue morcellators rapidly cut tissue into a plurality of fine particles. In other endoscopic surgical procedures, it is often necessary or desired to enclose a fractured organ during surgical repair to aid the surgeon in maintaining the integrity of the bodily organ.

U.S. Pat. No. 5,143,082 discloses a surgical device for enclosing body tissue or internal organs. The device consists of a plastic pouch having a cinch and loop which is mounted to the distal end of a cannula. The pouch is folded about the cannula and mounted in an introducer which is inserted through a conventional cannula into a body cavity during an endoscopic procedure. The pouch is unfurled in the body cavity. After body tissue has been placed in the cavity, the open end of the pouch is cinched closed and the tissue, bag and cannula are removed from the body cavity.

Conventional surgical pouches or bags for use in endoscopic procedures are typically made from plastic and shipped in a folded or rolled configuration (within an introducer) so that the surgeon may insert the pouch through a cannula without having to interrupt surgery to fold or roll the pouch during the operative procedure. It is known that most plastics when folded or rolled take a set. The effect of a "set" is to prevent the pouch from unfurling or unfolding and attaining a substantially flat configuration similar to that which it had prior to rolling or folding. It is preferred in an endoscopic procedure that the pouch have a substantially flat configuration to permit easy tissue insertion. It is often necessary to use a second endoscopic instrument to unfurl the pouch. This is not only time consuming, but requires the use of a second trocar cannula and at least one grasping instrument to maintain the pouch in a substantially flat configuration. Another deficiency which has been observed with conventional plastic pouches is that the mouth (or opening) of the pouch may be difficult to open in a body cavity, particularly when it becomes moist from body fluids. It is believed that the surface tension of the moisture in contact with the plastic of the pouch causes the mouth of the pouch to resist opening. Even when the mouth is dry, it often may be necessary to force it open by inserting an additional instrument into the mouth of the pouch and manipulating it to the full open position. After opening, difficulties with tissue insertion can develop because the mouth may re-close. When the mouth of the pouch becomes wet with body fluids, it is even more difficult to open the pouch because, it is believed, of the forces resulting from the surface tension of the fluids.

There is a need in this art for endosurgical pouches which unfold or unfurl automatically when inside of a mammalian body. There is also a need for endosurgical pouches which have mouths which open automatically when inside of a mammalian body.

DISCLOSURE OF THE INVENTION

Therefore, it is an object of the present invention to provide an endoscopic pouch which unfurls automatically in a body cavity.

It is a further object of the present invention to provide an endoscopic pouch which has a mouth which opens automatically when inserted into a body cavity.

Accordingly, an endosurgical pouch device is disclosed. The endosurgical pouch device has a strand having a distal loop means having an opening. The loop means is secured with a cinch means. The strand has a proximal free end portion and the cinch means is configured in a manner to allow movement of the free end portion proximally and to prevent the loop means from loosening when tightened. The free end portion of the strand is slidably mounted in a longitudinal tubular member having a longitudinal passage therethrough. A surgical pouch having an open end therein is mounted along substantially the entire perimeter of the open end to the loop means of the strand. The endosurgical pouch device has a means for pulling the free end portion of the strand proximally so as to continually reduce the opening of the loop means, thereby correspondingly closing the open end of the surgical pouch. The means for pulling may include a frangible proximal portion of the longitudinal tubular member to which the proximal end of the strand is mounted. The surgical pouch has a means for automatically unfurling or unfolding the pouch when the pouch is inserted into a body cavity. There is also a means for automatically opening the open end of the pouch when the pouch is inserted into a body cavity. The means for unfurling the surgical pouch preferably include a shape memory effect metal insert which is inserted into the pouch. Additionally, the means for automatically opening the mouth of the pouch include a strand and/or loop means made from a shape memory effect metal. The shape memory effect metal insert and loop means are designed to activate when equilibrated with a temperature approximately equal to mammalian body temperature.

Another aspect of the present invention is an endosurgical pouch device having a strand with a distal loop means having an opening. The loop means is secured with a cinch means. The strand has a proximal free end portion and the cinch means is configured in a manner to allow movement of the free end portion proximally and to prevent the loop means from loosening when tightened. The free end portion of the strand is slidably mounted in a longitudinal tubular member having a longitudinal passage therethrough. A surgical pouch having an open end therein is mounted along substantially the entire perimeter of the open end to the loop means of the strand. The endosurgical pouch has a means for pulling the free end portion of the strand proximally so as to continually reduce the opening of the loop means, thereby correspondingly closing the open end of the surgical pouch. The means for pulling may include a frangible proximal portion of the longitudinal tubular member to which the proximal end of the strand is mounted. The surgical pouch has a means for automatically unfurling or unfolding the pouch when the pouch is inserted into a body cavity. The means for unfurling the surgical pouch preferably include a shape memory effect metal insert which is inserted into the pouch. The shape memory effect metal insert is designed to activate when equilibrated with a temperature approximately equal to mammalian body temperature.

Yet another aspect of the present invention is an endosurgical pouch device. The endosurgical pouch device has a strand with a distal loop means having an opening. The loop means is secured with a cinch means. The strand has a proximal free end portion and the cinch means is configured in a manner so as to allow movement of the free end portion proximally and to prevent the loop means from loosening when tightened. The free end portion of the strand is slidably mounted in a longitudinal tubular member having a longitudinal passage therethrough. A surgical pouch having an open end therein is mounted along substantially the entire perimeter of the open end to the loop means of the strand. The endosurgical pouch device has a means for pulling the free end portion of the strand proximally so as to continually reduce the opening of the loop means, thereby correspondingly closing the open end of the surgical pouch. The means for pulling may include a frangible proximal portion of the longitudinal tubular member to which the proximal end of the strand is mounted. The surgical pouch has a means for automatically opening the open end or mouth of the pouch when the pouch is inserted into a body cavity. The means for automatically opening the mouth of the pouch include a strand and/or loop means made from a shape memory effect metal. The shape memory effect metal is designed to activate when equilibrated with a temperature approximately equal to mammalian body temperature.

Yet another aspect of the present invention is a method for performing an endosurgical procedure using any of the above-identified endosurgical pouches to enclose body tissue.

Another aspect of the present invention is a surgical pouch. The surgical pouch comprises a bag having an open end for access into the interior. The pouch may have means for automatically unfurling the bag, automatically opening the bag, or both automaticaly opening and unfurling the bag.

Other features and advantages of the present invention will become more apparent from the following description and accompanying drawings.

BRIEF DESCRIPTION OF THE DRAWINGS

FIG. 6 is a perspective view of the endoscopic surgical pouch of the present invention in a body cavity; the pouch is seen to contain body tissue with the mouth (or open end) of the pouch cinched closed.

FIG. 7 is a partial cross-sectional view of the proximal end of the cannula of the endosurgical pouch device.

FIG. 8 is a partial plan view of the endosurgical pouch device including a partial plan view of the distal end of the cannula with a partial cut-away of the endosurgical pouch showing a shape memory effect metal insert.

FIG. 9 is a partial cross-sectional view of the endosurgical pouch and the loop.

FIG. 10 is an exploded perspective view of the endosurgical pouch device of the present invention.

BEST MODE FOR CARRYING OUT THE INVENTION

As defined in this application, the word "distal" is used, conventionally, to describe that portion of the device which extends away from the user during use, and the word "proximal" is used, conventionally, to describe that portion of the device that extends toward the user during use.

Figure 11:
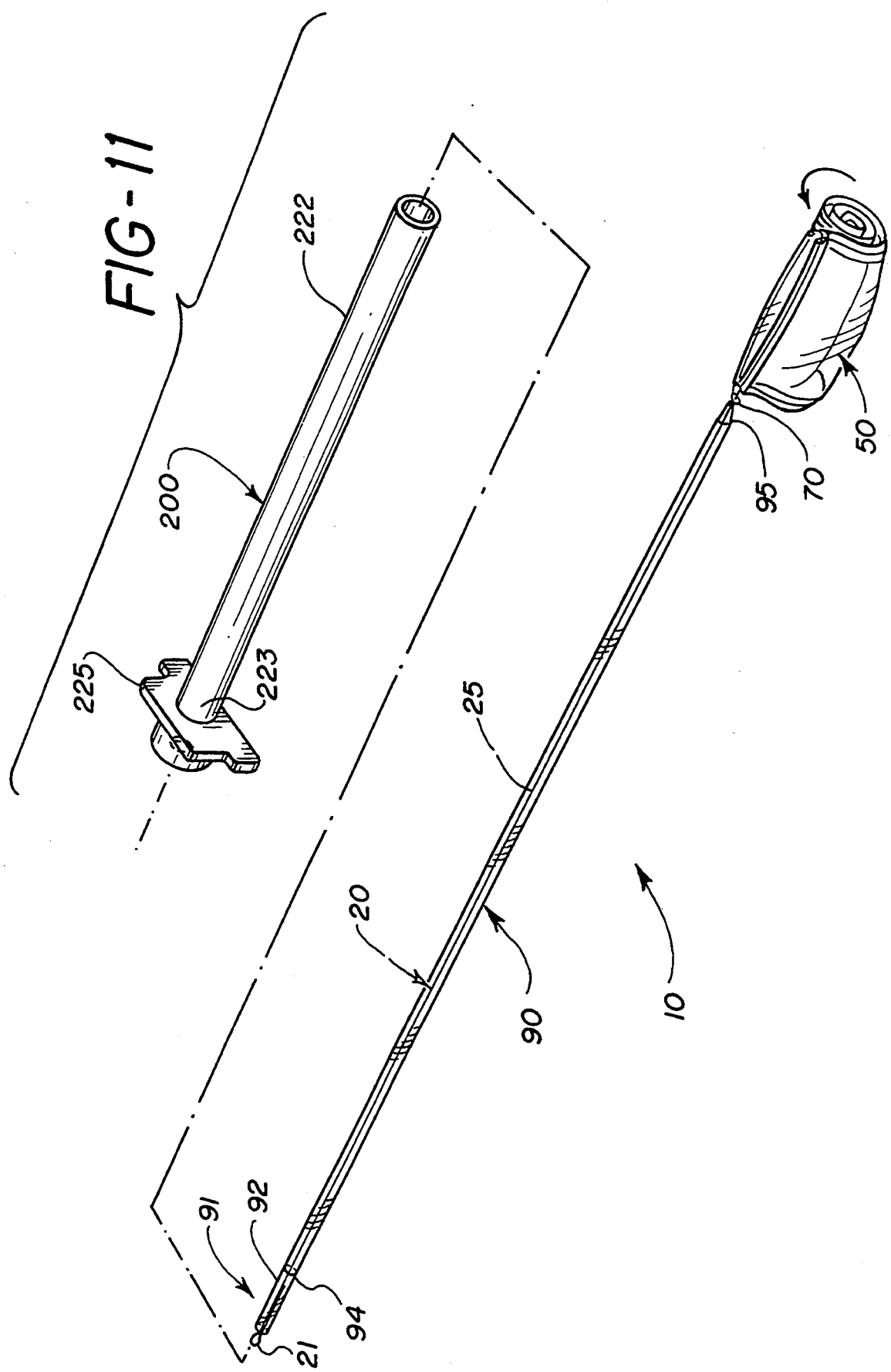
FIG. 11 is a perspective view of the endosurgical pouch device and an introducer.
Figure 12:
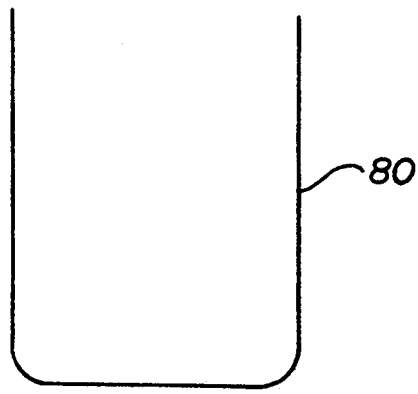
FIG. 12 is a plan view of an insert for an endosurgical pouch of the present invention having a squared bottom.
Figure 13:
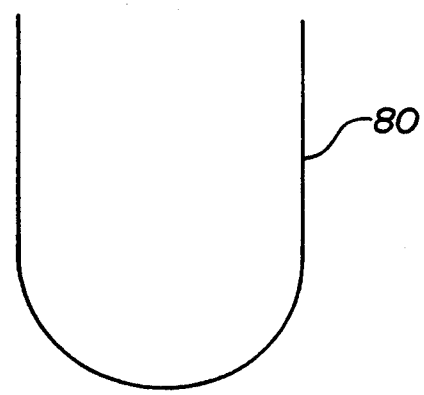
FIG. 13 is a plan view of an insert for an endosurgical pouch of the present invention having a rounded bottom.
Figure 14:
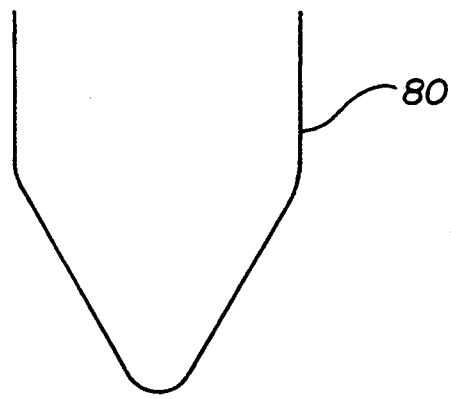
FIG. 14 is a plan view of an insert for an endosurgical pouch of the present invention having a triangularly shaped bottom section.
Figure 15:
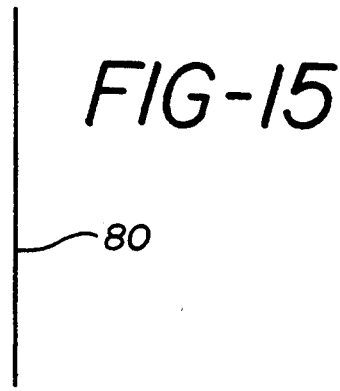
FIG. 15 is a plan view of a linear insert for an endosurgical pouch of the present invention wherein the an insert is mounted along a single side of the pouch.

Referring to the Figures, an endosurgical pouch device 10 representing a preferred embodiment of this invention is seen in FIG. 10 and FIG. 11. The device 10 includes a strand 20 having a distal noose or loop portion 30 and a proximal free end portion 25.

Strand 20 can be prepared from any conventional surgical suture material, e.g. nylon, silk, steel, catgut, and conventional bioabsorbable suture materials such as polymers and copolymers of lactide, glycolide, paradioxanone and trimethylene carbonate. However for purposes of the present invention it is particularly preferred to have a strand 20 made from a shape memory effect metal. It is required that the loop portion 30 be made from a shape memory effect metal whenever the endosurgical pouch device 10 has a pouch 50 with automatic mouth opening capability. Shape memory effect (SME) metals will be discussed more extensively further in the specification. When the free end portion 25 is made from a conventional suture material, the free end portion 25 is joined to loop portion 30 to form strand 20 using conventional techniques including knots, mechanical couplers, adhesives and the like.

Referring to FIGS. 3-6 and 8-11, a surgical pouch 50 is seen to be a bag having an open end or mouth 55 for access into the interior of pouch 50 for placement of tissue or organs. Pouch 50 is seen to be attached at its upper end 52 to loop portion 30 along substantially the entire perimeter of the open end or mouth 55 of the pouch by engagement with substantially the entire length of distal loop portion 30. The bottom 54 of pouch 50 is seen to be closed.

The free end portion 25 of strand 20 is slidably mounted within a generally rigid, longitudinal tubular sleeve 90, often referred to in this art as a cannula. Tubular sleeve 90 has an optional frangible portion 92 at its proximal end 91. An optional score line 94 is disposed distally to the proximal end 91 to form the frangible portion 92. The proximal end 21 of strand 20 is optionally fixedly mounted within the frangible portion 92 of the tubular sleeve 90 using conventional mounting methods, e.g., bonding with a conventional adhesive such as an epoxy, mechanically by using a fastener, ultrasonic welding and the like.

As illustrated in more detail in FIGS. 3-5 and 8, the loop portion 30 of strand 20 is contained within a channel 57 running along all, or substantially all, of the circumferential length of the open end or mouth 55 of the surgical pouch 50. In this embodiment, channel 57 is formed by folding the top, upper portion 52 of the pouch 55 over about itself to form a flap 56 (or flaps 56), and then sealing the folded-over flap 56 (or flaps 56) to pouch 50 to create channel 57. In a like manner, pouch 50 can also have an optional edge channels 62 and an optional bottom channel 64. The edge channels 62 and bottom channel 64 can be formed by conventional methods including heat sealing, ultrasonic welding and the like. Pouch 50 can be mounted to loop portion 30 using conventional mounting means effective to allow the mouth 55 of pouch 50 to be cinched closed. The mounting means may include eyelets, loops and the like.

The loop portion 30 of strand 20 is secured with a cinch means 70, which allows sufficient movement of strand 20 proximally through cinch means 70 to effectively close loop 30 and mouth 55 of pouch 50, and, to both prevent the loop portion 30 from loosening and the mouth 55 from opening after the loop 30 and mouth 55 have been closed. Longitudinal tubular sleeve 90 is seen to have a tapered distal end 95 which prevents cinch means 70 and loop 30 and pouch 50 from passing through the interior passage 99 of tubular sleeve 90 during use. Loop portion 30 is seen to have opening 35 which varies in size as strand 20 is moved proximally through and cinch means 70.

Figure 16:
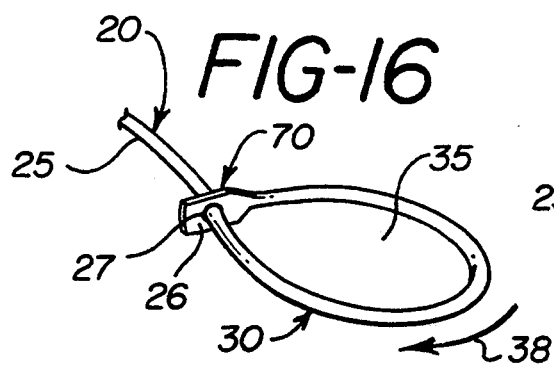
FIG. 16 is a perspective of a cinched loop of the present invention wherein the cinch means is formed by flattening an end of a strand and drilling a hole through it and passing the strand through the hole.
Figure 17:
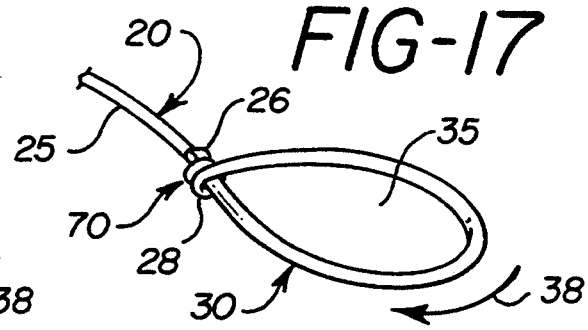
FIG. 17 is a perspective view of an embodiment of the cinch means and loop means wherein the cinch means is formed by wrapping an end of a strand several times about itself.
Figure 18:
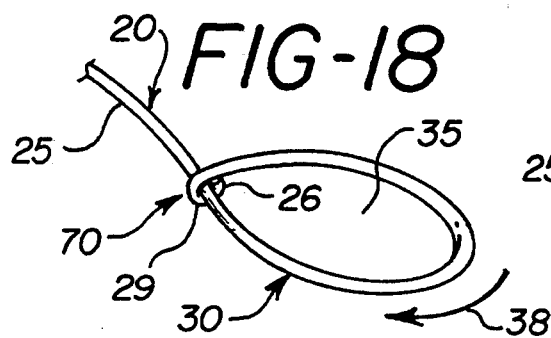
FIG. 18 is a perspective view of another embodiment of the cinch means and loop means wherein the cinch means is formed by attaching an eyelet to an end of a strand.
Figure 19:
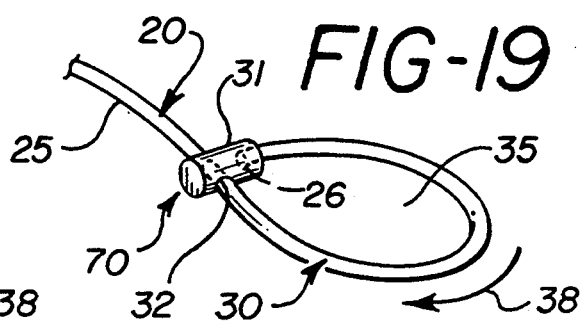
FIG. 19 is perspective view of still yet another embodiment of the cinch means and loop means wherein a cylindrical member is attached to an end of a strand and the strand is passed through a transverse hole in the member.

Referring to FIGS. 16-19, various configurations of cinch means 70 can be seen. In FIG. 16, cinch means 70 is formed by flattening the distal end 26 of strand 20 and drilling a hole 27 therethrough. Then, the proximal end 21 of strand 20 is threaded through hole 27 and loop 30 and free end 25 are thereby formed. Referring to FIG. 17, it is seen that the cinch means 70 is formed by wrapping the distal end 26 about strand 20 several times to form a knot-like structure 28 and loop 30. Strand 20 is then free to move through knot-like structure 28. Referring to FIG. 18, cinch means 70 is seen to be formed by bending the distal end 26 of strand 20 to form a single eyelet, and then threading the remainder of strand 20 beginning with proximal end 21 through the eyelet 29 to form the loop 30 and the free end 25. Alternately, an eyelet could be attached to the distal end 26 of strand 20 and the loop 30 could be formed in a similar manner. The eyelet can be secured by conventional methods including brazing, spot welding and the like. Referring now to FIG. 19, another embodiment of the cinch means 70 of the present invention is seen. In this embodiment, a cylindrical member 31 is attached to the distal end 26 of the strand 20. The cylindrical member 31 has a transverse opening 32 therethrough. The distal end 21 of strand 20 is threaded through the transverse hole 32 and the loop 30 and free end 25 are thereby formed. The loop 30 in each of FIGS. 16-19 is seen to have the inner opening 35. As the loops 30 in FIGS. 16-19 are tightened, the strand 20 will have a direction of movement as indicated by the arrows 38.

The surgical pouches 50 of the present invention may have an insert 80 (when having automatic unfurling capability) as seen in FIG. 10 and FIGS. 12-15. The insert 80 will be a shape memory effect metal insert having a variety of configurations as illustrated in FIGS. 12–15. The insert 80 may have a variety of configurations ranging from a substantially rectangular shape having rounded corners to a U-shape. The insert may also have a V-shape or may comprise a single linear member inserted into the pouch. The inserts 80 will preferably be made from a wire which is in turn manufactured from a shape memory effect metal. The inserts 80 may be simply placed into the pouch 50 or may be placed into specially formed pockets or channels, such as channels 62 and 64, in the pouch 50 for receiving the inserts 80. The inserts 80 will be sufficiently rigid to effectively maintain a pouch 80 in a substantially flat configuration.

Surgical pouch 50 may be constructed of a wide variety of materials, but generally the material used should be biocompatible and non-toxic to body tissue. In addition, the material should exhibit sufficient conformability so that it can effectively fit down a trocar. If the endosurgical pouch device 10 is to be used to morcellate and/or remove tissue, then the pouch 50 is desirably waterproof to prevent tissue and fragments of tissue from escaping. Additionally, for this application, the pouch 50 should be sufficiently constructed so as to effectively have a high tear and burst resistance, a low modulus and moderate elongation. Although a variety of conventional materials can be used for this purpose, a preferred material of construction for the surgical pouch 50 is PEBAX® block copolyetheramide. Alternatively, if the pouch 50 is to be used for encapsulating, for example, a fractured organ during surgical repair, then it may be desirable to employ a pouch 50 made from a material having a mesh network. See, for example, U.S. Pat. No. 4,428,375, which is incorporated by reference and describes a variety of pliable surgical materials well known in the art for this application that can be fabricated into a desired mesh structure.

The endosurgical pouch device 10 may be constructed with both automatic pouch 50 unfurling means such as insert 80 and automatic mouth 55 opening means such as loop 30 made from a shape memory effect metal. If desired, the device 10 may have only automatic unfurling means or only automatic mouth 55 opening means.

The pouches 50 of the present invention may be used if desired, without cannula 90. In such a case, the pouch 50 may have a shape memory effect metal insert 70 for automatic unfurling, a shape memory effect loop 30 mounted to the open end of the pouch 55 for automatic opening, or both a shape memory effect insert 70 and loop 30. When using pouch 50 in an endosurgical procedure without a cannula 90, the bag may be rolled and inserted into an introducer 200, and then placed within a body cavity. The pouch 50 is manipulated within the body cavity using conventional endosurgical instruments.

Figure 1:
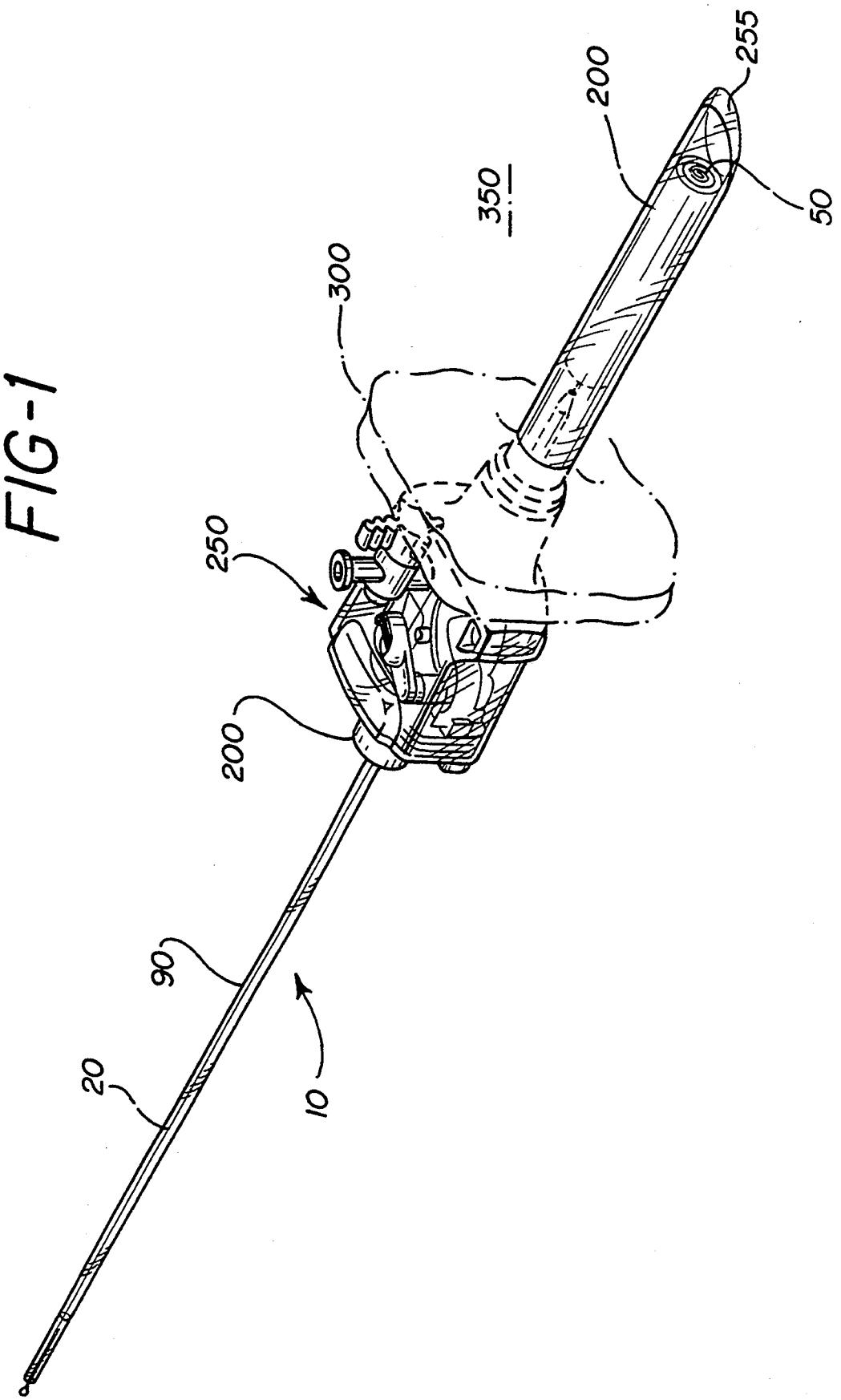
FIG. 1 is a perspective view of the endoscopic pouch device of the present invention in an introducer being inserted through a trocar cannula into a body cavity.
Figure 2:
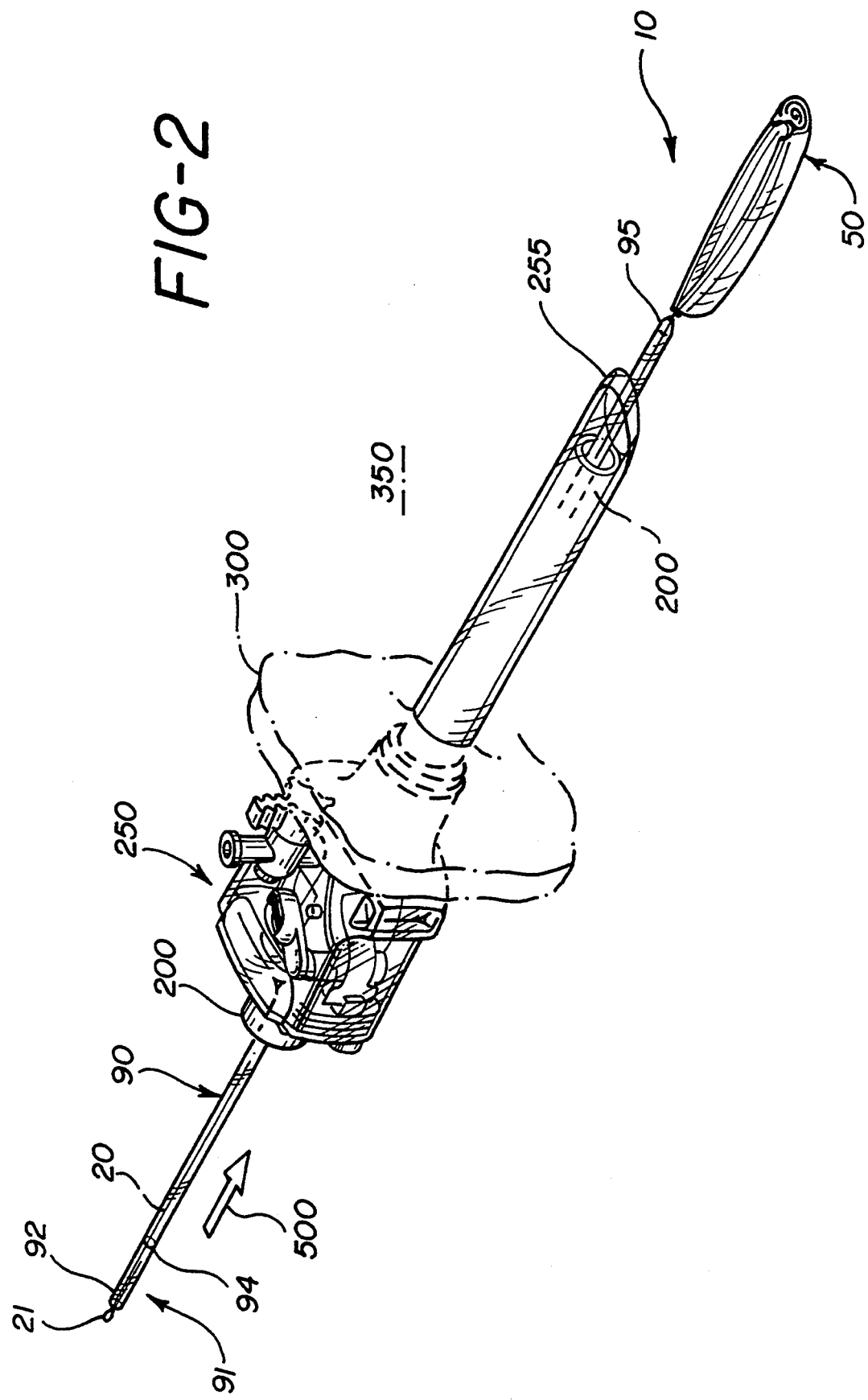
FIG. 2 is a perspective view of the endoscopic surgical pouch of the present invention immediately after exiting the distal end of the introducer and the distal end of the trocar cannula into a body cavity and prior to unfurling.
Figure 3:
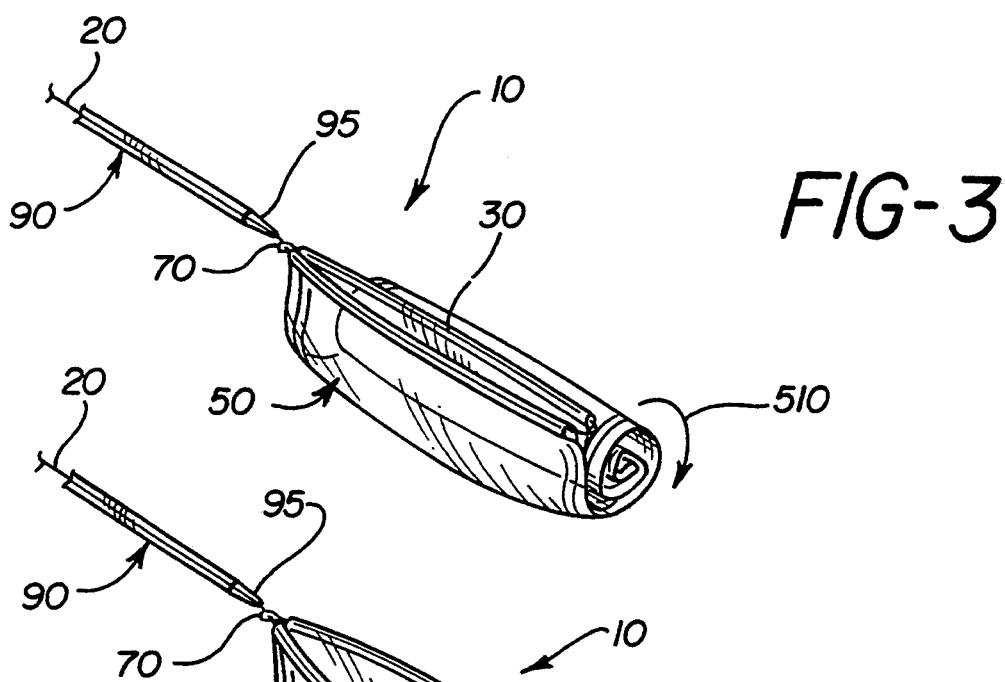
FIG. 3 is a perspective view of the endoscopic surgical pouch of the present invention after insertion into a body cavity and illustrating the pouch with the mouth of the pouch closed prior to unfurling.
Figure 4:
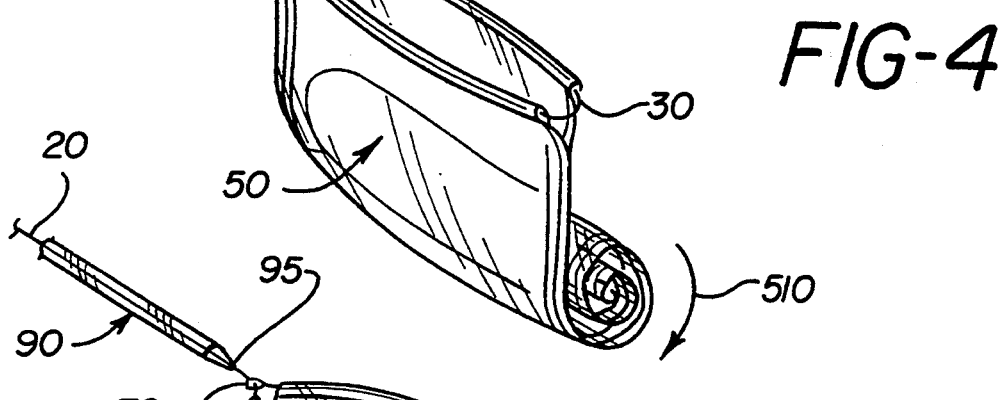
FIG. 4 is a perspective view of the pouch of the present invention opened in a semi-unfurled configuration with the mouth of the pouch partially opened.
Figure 5:
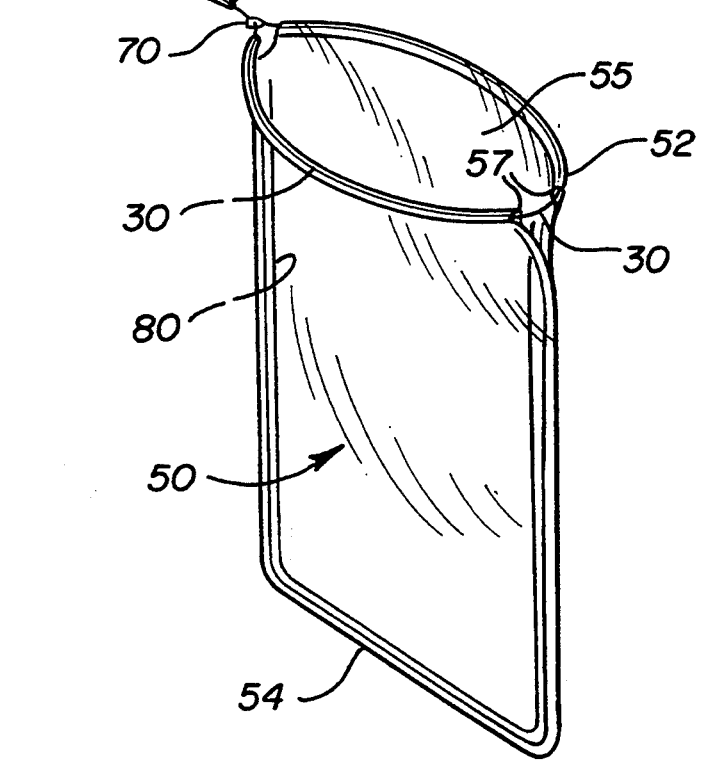
FIG. 5 is a perspective view of the endoscopic surgical pouch of the present invention in a completely unfurled configuration with the mouth of the pouch completely open.

Referring now to FIGS. 1–6 in combination, one can see generally how the endosurgical pouch device 10 is used to enclose body tissue 400. Initially, the endosurgical pouch 10, contained within a conventional introducer 200, is inserted into a conventional trocar cannula 250. The trocar cannula 250 would have been previously emplaced through a body wall 300 into a body cavity 350 using a conventional trocar obturator. Then, the endosurgical pouch device 10 is displaced distally in the direction of arrow 500 through the introducer 200 and exits the distal end 255 of cannula 250 as seen in FIG. 2. Referring now to FIGS. 3,4, and 5, after the pouch 50 and distal end 95 of cannula 90 exit trocar cannula 250, the mouth 55 of pouch 50 begins to open and the pouch 50 begins to unfurl in the direction of arrow 510. As the temperature of loop 30 and insert 80 equilibrate with the patient's body temperature (and the metal becomes austenitic), the shape memory effect will cause the insert 80 to substantially straighten out thereby causing the pouch 50 to unfurl and also causing the loop 30 to open thereby causing the mouth 55 to open. In order to encapsulate body tissue 400, as seen in FIG. 6, the surgeon would first grip optional frangible portion 92 of tubular sleeve 90 with one hand and the remaining portion of tubular sleeve 90 with the other hand, and then snap apart the two pieces about optional score line 94 (See FIG. 7). This allows for the strand 20 to be retracted proximally in the direction of arrow 520 through the interior passage 99 of longitudinal tubular sleeve 90 by pulling proximally on optional frangible portion 92. If no optional frangible portion 92 is present, the surgeon would merely pull proximally on free end 25 of strand 20. Following this simple procedure, the user could then place the surgical pouch 50 about body tissue 400 by positioning the pouch 50 at the appropriate location about the body tissue 400. To complete the procedure, strand 20 is pulled proximally as shown by the arrow 520 in FIG. 6, causing the distal loop portion 30 of strand 20 to close the open end or mouth 55 of surgical pouch 50 as the strand 20 is drawn through the cinch means 70. If desired, frangible end 92 can be fractured after placement of tissue 400 in pouch 50. As shown in FIGS. 6 and 8, cinch means 70 is restrained by tapered end 95 of the longitudinal tubular sleeve 90 while the surgeon is pulling strand 20 proximally thereby allowing strand 20 to pass through the interior passage 99 of tubular sleeve 90 so that the distal loop portion 30 may be closed about body tissue 400. The cinch means 70 configuration should be such that once the distal loop portion 20 is closed about body tissue 150, loop portion 20 effectively remains closed and does not loosen.

Referring now to FIGS. 1–5, and 11 the endosurgical pouch device 10 is typically used in combination with introducer 200 and trocar cannula 250 to facilitate its use during endoscopic surgery. Introducer 200 is seen to have tube 222. The proximal end 223 of tube 222 is mounted to handle 225. The surgical pouch 50 is rolled about the longitudinal axis of the loop 30 of strand 20 so as to facilitate the insertion of the endosurgical pouch device 10 into introducer 200 which is then inserted into an appropriately sized trocar cannula 250 for insertion into a desired body cavity 350. As shown in FIGS. 1 and 2, the trocar cannula 250 is introduced into a desired body cavity 350 by penetration of the body cavity wall 300 surrounding body cavity 350. As shown in FIGS. 1–6, once the trocar cannula 250 is appropriately placed, the endosurgical pouch device 10 of this invention can be maneuvered distally through trocar cannula 250 so as to cause surgical pouch 50 to exit from introducer 200 and cannula 250 and into body cavity 350. Once pouch 50 is placed within body cavity 350 free of the confines of the trocar cannula 250 and introducer 200, it can automatically unfurl and mouth 55 can automatically open as shown in FIGS. 3–5. After surgical pouch 50 unfurls, the surgeon can then manipulate the endosurgical pouch device 10 so as to place unfurled surgical pouch 50 having open mouth 55 about a section of desired body tissue 400. The surgeon can perform the procedure outlined above to capture and secure the tissue 400 in the pouch 50.

Following the completion of the surgical procedure, the pouch 50 can either be removed from the body cavity 350 or left intact at the surgical site, depending on the operative procedure performed. For example, if body tissue 400 is morcellated within the pouch 50, and therefore it becomes necessary to remove the fragmented tissue 400 from the body cavity 350, then the pouch 50 can be readily removed by pulling the tubular sleeve 90 and pouch 50 proximally through the introducer 200 and trocar cannula 250 until the entire endosurgical pouch device 10, including pouch 50, has been removed from the body cavity 350. Alternatively, if pouch 50 is composed of a bioabsorbable surgical mesh, and the pouch 50 is used to facilitate the repair of a damaged organ over an extended period of time, it may be desirable to leave pouch 50 intact at the surgical site. This can be accomplished simply by first cutting strand 20 at or near the junction of distal loop portion 30 and free end portion 25, and then pulling tubular sleeve 90 proximally so as to remove the loop portion 30 and free end portion 25 of strand 20 from trocar 250 while leaving pouch 50 intact within the body cavity 300.

The surgical procedures described above can also be performed in a similar manner with a device 10 having only automatic pouch 50 unfurling means and no automatic mouth 55 opening means, or, vice versa, only automatic mouth 55 opening means and no automatic pouch 50 unfurling means.

The strand 20 will be preferably be made from a single filament, shape memory effect metal having sufficient shape memory effect (SME) properties, biocompatibility properties and mechanical properties to effectively open a mouth 55 of a pouch 50, although only the loop portion 30 may be made from the SME metal. The insert 80 will also be made from a SME alloy having sufficient SME properties, biocompatibility properties and mechanical properties to effectively unfurl a pouch 50. The term metal is defined to include metal alloys. The shape memory effect metals useful to form the wires 20 of the present invention will typically be made from alloys having the following compositions: Nickel-titanium with 50% nickel or less, Nickel-titanium-platinum alloys with below about 15% platinum, and nickel-titanium-palladium alloys with below about 18% palladium. It is preferred to use the nickel-titanium alloys which are often referred to as shape memory effect alloys. The shape memory effect metals used in the practice of the present invention will preferably transform to a austenitic state at human body temperature.

The basis of the Shape Memory Effect (SME) is a phase change that takes place in certain alloys; i.e. shape memory alloys (SMAs), as they are cooled or heated through their characteristic transformation temperature. The best known SMAs are NiTi (Nitinol) alloys in which the phase change is from an ordered cubic crystal form above its transformation temperature (TTR) to a monoclinic crystal phase below the TTR. The transformation is known as a martensitic transformation between a high temperature "austenitic" form and a low temperature "martensitic" form. For a given alloy composition in a given annealed condition, the transformation takes place at a predictable, repeatable temperature. The transformation takes places when the alloy in one phase reaches a temperature at which the other phase is thermodynamically more stable. Because the change takes place by a shearing motion of the above, instead of by a diffusion mechanism, the transformation takes place virtually instantaneously.

Note that it is convenient to refer to a single TTR at which the phase transformation takes place. More precisely, an alloy becomes martensitic over a narrow temperature range as it is cooled through TTR and becomes austenitic over a narrow, and slightly higher temperature range as it is heated through TTR.

Figure 20:
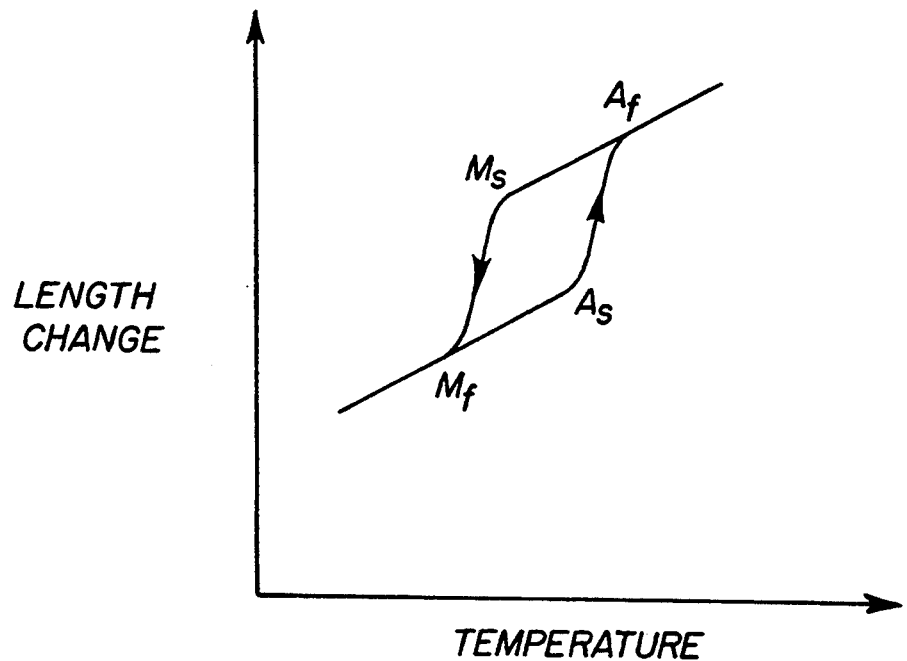
FIG. 20 is a graphical plot of property changes versus temperature showing the transformation temperatures As, Af, Ms, Mf for a typical shape memory effect metal.

A conventional hysteresis curve, as shown in FIG. 20, depicts this behavior. On heating the alloy, the transformation to the high temperature austenitic phase begins at a temperature equal to $A_s$ and is complete at a temperature equal to $A_f$. On subsequent cooling, the alloy begins the martensitic transformation at a temperature equal to $M_s$ and completes it at a temperature equal to $M_f$. In order to induce in the alloy a shape that will be remembered, the alloy must be trained by constraining it in the desired shape and heating it to a temperature well above $A_f$.

Figure 21:
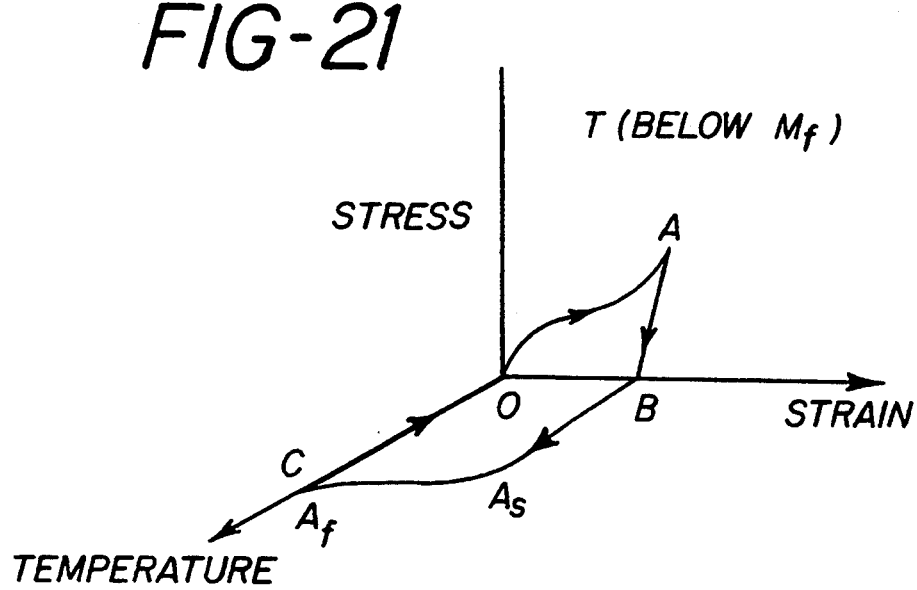
FIG. 21 is a three dimensional stress-strain-temperature graphical diagram showing the shape memory effect.

Another way of viewing the behavior of SMAs uses a stress/strain/temperature curve as shown in FIG. 21. Beginning with the alloy in its remembered shape and martensitic phase at an origin "O", the alloy is deformed along a path O–A. When the deformation is complete (i.e. stress removed), the alloy relaxes slightly along a curve A–B. Heating the alloy to the austenitic phase returns it (nearly) to its original shape along a curve B–C.

The use of SMA's for the strands 20, the loops 30 and inserts 80 is as follows. A strand 20, loop 30 or insert 80 is fabricated from a SMA into the desired shape using conventional forming techniques. The shape is maintained at a temperature well above $A_f$ in the austenitic phase, e.g., 500° C. The strand 20, loop 30 or insert 80 is then cooled below $M_f$, transforming to the martensitic phase. While in the martensitic phase, the strand 20, the loop 30 or insert 80 is deformed to the extent necessary for insertion into the introducer 200.

At the surgical site, the loop 30 and insert 80 are heated from a temperature at or below $A_s$ to a temperature above $A_f$ by conducting heat from the patient's body cavity. Thus, the alloy used for SME loop 30 and inserts 80 preferably undergoes its phase transformation in a narrow range near normal body temperature. The alloy is preferably austenitic above about 35°. ($A_f$=35° C.). If the insert 80 and loop 30 temperature rises above $A_s$ during storage, shipment, or insertion through the cannula, they would undesirably tend to assume their memory shape prematurely. This tendency can be counteracted by refrigeration and/or maintaining the insert 80 and, strand 20 and/or loop 30 in a constrained manner prior to use, for handling convenience $A_s$ is preferably about 25° C. or more.

A variety of SMAs have been identified that are suitable to a greater or lesser degree for SME inserts 80 and strands 20 and loops 30 of the present invention. Preferred alloys comprise nickel and at least one of aluminum, cobalt and titanium, in which the low temperature state is martensitic and the high temperature state is austenitic. Among these are Nitinol alloys, which are primarily nickel and titanium (generally about 50% each), but may also include small amounts of platinum or palladium.

The following examples are illustrative of the principles and practice of the present invention although not limited thereto.

EXAMPLE 1

An animal of conventional size and weight was prepared for endoscopic surgery in a conventional manner. The patient was anaesthetized with a sufficient dose of a conventional anesthetic to induce an anaesthetic state and then an endotracheal tube was placed and connected into a conventional anesthesia machine to allow the animal to be ventilated as required. The surgical site was prepared in a conventional manner including depilation of epidermis in the region of expected incision, scrubbing and rinsing with conventional fluids and application of a conventional iodine solution. The animal was placed in a reclining position on a conventional surgery table and draped with a sterile drape. The abdominal cavity of the animal was insufflated in a conventional manner with carbon dioxide and five conventional trocars were inserted into the abdominal cavity. Using conventional laparoscopic surgical instruments and suture material, the blood supply to the ovaries and uterus was ligated. Once all blood supply to the ovaries and uterus was interrupted they were cut free from all of their connections using conventional laparoscopic instruments.

A conventional introducer 200, containing the endosurgical pouch device 10, was placed into one of the conventional trocar cannulas 250. The endoscopic pouch device 10 was then advanced into the abdominal cavity until the entire pouch 50 was free of the cannula 250. The shape memory effect metal insert 80 and loop portion 30 of the endoscopic pouch 50, when exposed to conventional body temperature, returned to their preshaped configurations, which both opened the mouth of the pouch 50 and unfurled the length of the pouch 50 to substantially straight configurations. The uterus and ovaries, which were being held in conventional laparoscopic surgical instrument, were then placed into the open pouch 50 through mouth 55. The mouth 55 of the pouch 50 was then closed by pulling the strand 20 thereby closing loop 30 which encircles the mouth 55 of the pouch 50. The endosurgical pouch device 10 and pouch 50 and its contents were removed from the body through the trocar cannula.

EXAMPLE 2

A human patient is prepared for surgery using conventional preparatory techniques and is effectively anesthetized using a sufficient dose of a conventional anesthetic. After an endotracheal tube is placed, the patient is connected to conventional anesthesia equipment, and as needed, ventilated. Using conventional endoscopic preparatory procedures, including insufflation and insertion of an endoscope, three trocars are inserted into the abdominal cavity.

Using conventional laparoscopic surgical instrumentation and conventional laparoscopic surgical techniques, a piece of tissue to be removed is freed from a tissue bed and held in conventional endoscopic graspers. A conventional endoscopic introducer 200, containing the endoscopic pouch device 10, is inserted into one of the three trocar cannulas 250. The endoscopic pouch device 10 is then advanced out of the cannula until the pouch 50 is entirely free of the cannula. The shape memory effect of the metal insert 80 and the loop 30, when exposed to conventional body temperature, return to their preshaped configurations, which both opens the mouth 55 of the pouch 50 and unfurls the length of the pouch 50 to a substantially straight configuration. The graspers holding the tissue are then advanced toward and then into the open mouth 55 of the pouch 50. By opening the graspers and removing them from the pouch 50, the tissue is now left in the pouch 50. The mouth 55 of the pouch 50 is then cinched closed by pulling on the wire strand 20 and loop 30 which surrounds the opening of the pouch 50, and the endoscopic pouch device 10 with the tissue secured within pouch 50 is removed from the body through the trocar cannula 250.

The endosurgical pouch device 10 of the present invention have numerous advantages. When inserted into a mammalian body cavity, the pouch 50 automatically unfurls and the mouth 55 automatically opens. This eliminates the need for a second endosurgical instrument to unfurl the pouch 50 and open the mouth 55 in the body cavity. This allows a trocar cannula to be freed for other instruments and may improve the efficiency of the surgical procedure.

Although only the most preferred surgical device of this invention is described herein, numerous additional embodiments will become apparent to those skilled in this art, all of which are well within the scope and spirit of the claimed invention.

What is claimed is:

1. An endosurgical pouch device comprising:
   (a) a longitudinal tubular member having a longitudinal passage therethrough, a distal end, and a proximal end;
   (b) a strand having a distal loop means, said loop means having an opening secured with cinch means, the strand having a proximal free end portion, said free end portion slidably mounted within the tubular member, said cinch means configured in a manner so as to allow movement of the free end portion proximally and to prevent the loop portion from loosening when tightened;
   (c) a surgical pouch having an open end therein, said pouch attached along substantially the entire perimeter of said open end thereof to said loop portion of said strand;
   (d) means for pulling said free end portion of said strand proximally so as to continually reduce the opening of the loop portion thereby continually closing said open end of said surgical pouch;
   (e) means for automatically unfurling said pouch when the pouch is inserted furled into a body cavity, said unfurling means mounted in the pouch and wherein said unfurling means comprises a shape memory effect metal insert; and
   (f) means for automatically opening said open end of said pouch when the pouch is inserted into a body cavity said automatic opening means mounted to the pouch, wherein said opening means compresses said distal loop means made from a shape memory effect metal, wherein said cinch means abuts the distal end of the tubular member when said free end portion of said strand is pulled proximally, and the passage through the distal end of the tubular member has a cross-section effective to prevent said cinch means from passing through said tubular sleeve when said free end portion of said strand is pulled proximally.

2. The endosurgical pouch device of claim 1 wherein the shape memory effect metal insert comprises Nitinol.

3. The endosurgical pouch device of claim 1 wherein the shape memory effect metal loop comprises Nitinol.

4. The endosurgical pouch device of claim 1 wherein said tubular sleeve has a frangible portion at its proximal end.

5. The endosurgical pouch device of claim 4 wherein a score line is disposed at the distal end of said frangible portion.

6. The endosurgical pouch device of claim 5 wherein said free end portion of said strand is securingly attached within said frangible portion of said tubular sleeve, whereby a user of said medical device can break said tubular sleeve about said frangible portion at said score line and pull proximally said frangible portion so as to pull said free end portion of said strand proximally.

7. The endosurgical pouch device of claim 6 wherein said free end portion is adhesively attached within said frangible portion with epoxy adhesive.

8. The endosurgical pouch device of claim 1 wherein said pouch comprises block copolyetheramide.

9. The endosurgical pouch device of claim 1 wherein said open end of said pouch is securingly engaged to said loop portion of said strand within a channel disposed along the top of said pouch about the open end.

10. The endosurgical pouch device of claim 1 wherein said pouch further comprises a closed bottom portion sealed by a peripheral edge seal.

11. The endosurgical pouch device of claim 1 wherein the strand comprises a shape memory effect metal.

12. The endosurgical pouch of claim 11 wherein the strand comprises Nitinol.

13. An endosurgical pouch device comprising:
(a) a longitudinal tubular member having a longitudinal passage therethrough, a distal end, and a proximal end;
(b) a strand having a distal loop means, said loop means having an opening secured with cinch means, the strand having a proximal free end portion, said free end portion slidably mounted within the tubular member, said cinch means configured in a manner so as to allow movement of the free end portion proximally and to prevent the loop portion from loosening when tightened;
(c) a surgical pouch having an open end therein, said pouch attached along substantially the entire perimeter of said open end thereof to said loop portion of said strand;
(d) means for pulling said free end portion of said strand proximally so as to continually reduce the opening of the loop portion thereby continually closing said open end of said surgical pouch; and
(e) means for automatically unfurling said pouch when the pouch is inserted furled into a body cavity said unfurling means mounted in the pouch and wherein said unfurling means comprises a shape memory effect metal insert,
wherein said cinch means abuts the distal end of the tubular member when said free end portion of said strand is pulled proximally, and the passage through the distal end of the tubular member has a cross-section effective to prevent said cinch means from passing through said tubular sleeve when said free end portion of said strand is pulled proximally.

14. The endosurgical pouch device of claim 13 wherein said tubular sleeve has a frangible portion at its proximal end.

15. The endosurgical pouch device of claim 14 wherein a score line is disposed at the distal end of said frangible portion.

16. The endosurgical pouch device of claim 15 wherein said free end and portion of said strand is securingly attached within said frangible portion of said tubular sleeve, whereby a user of said medical device can break said tubular sleeve about said frangible portion at said score line and pull proximally said frangible portion so as to pull said free end portion of said strand proximally.

17. The endosurgical pouch device of claim 16 wherein said free end portion is adhesively attached within said frangible portion with epoxy adhesive.

18. The endosurgical pouch device of claim 13 wherein said pouch comprises of block copolyetheramide.

19. The endosurgical pouch device of claim 13 wherein said open end of said pouch is securingly engaged to said loop portion of said strand within a channel disposed along the top of said pouch about the open end.

20. The endosurgical pouch device of claim 13 wherein said pouch further comprises a closed bottom portion sealed by a peripheral edge seal.

21. The endosurgical pouch device of claim 13 wherein the strand comprises a shape memory effect metal.

22. An endosurgical pouch device comprising:
(a) a longitudinal tubular member having a longitudinal passage therethrough, a distal end, and a proximal end;
(b) a strand having a distal loop means, said loop means having an opening secured with cinch means, the strand having a proximal free end portion, said free end portion slidably mounted within the tubular member, said cinch means configured in a manner so as to allow movement of the free end portion proximally and to prevent the loop portion from loosening when tightened;
(c) a surgical pouch having an open end therein, said pouch attached along substantially the entire perimeter of said open end thereof to said loop portion of said strand;
(d) means for pulling said free end portion of said strand proximally so as to continually reduce the opening of the loop portion thereby continually closing said open end of said surgical pouch; and,
(e) means for automatically opening said open end of said pouch when the pouch is inserted into a body cavity said automatic opening means mounted to the pouch, wherein said opening means comprises said distal loop means made from a shape memory effect metal,
wherein said cinch means abuts the distal end of the tubular member when said free end portion of said strand is pulled proximally, and the passage through the distal end of the tubular member has a cross-section effective to prevent said cinch means from passing through said tubular sleeve when said free end portion of said strand is pulled proximally.

23. The endosurgical pouch device of claim 22 wherein the shape memory effect metal comprises Nitinol.

24. The endosurgical pouch device of claim 22 wherein said tubular sleeve has a frangible portion at its proximal end.

25. The endosurgical pouch device of claim 24 wherein a score line is disposed at the distal end of said frangible portion.

26. The endosurgical pouch device of claim 22 wherein said free end portion of said strand is securingly attached within said frangible portion of said tubular sleeve, whereby a user of said medical device can break said tubular sleeve about said frangible portion at said score line and pull said free end portion of said strand proximally.

27. The endosurgical pouch device of claim 26 wherein said free end portion is adhesively attached within said frangible portion with epoxy adhesive.

28. The endosurgical pouch device of claim 22 wherein said pouch comprises of block copolyetheramide.

29. The endosurgical pouch device of claim 22 wherein said open end of said pouch is securingly engaged to said loop portion of said strand within a channel disposed along the top of said pouch about the open end.

30. The endosurgical pouch device of claim 22 wherein said pouch further comprises a closed bottom portion sealed by a peripheral edge seal.

31. The endosurgical pouch device of claim 22 wherein the strand comprises a shape memory effect metal.

32. The endosurgical pouch device of claim 31 wherein the shape memory effect metal comprises Nitinol.

33. A surgical pouch, comprising;
a bag, for use with a cannula assembly having an open end for access into the interior of the bag; and
means for automatically unfurling the bag when furled around a cannula wherein the means for automatically unfurling the bag comprises a shape memory effect metal insert mounted in the surgical bag.

34. The surgical pouch of claim 33 wherein the shape memory effect metal comprises Nitinol.

35. A surgical pouch, comprising;
a bag having an open end for access into the interior of the bag; and,
means for automatically opening the open end of the bag wherein the means for opening the open end of the bag comprises a shape memory effect metal loop mounted to the open end of the bag.

36. The surgical pouch of claim 35 wherein the shape memory effect metal comprises Nitinol.

37. A surgical pouch, comprising;
a bag, for use with a cannula assembly having an open end for access into the interior of the bag;
means for automatically unfurling the bag when furled around a cannula wherein the means for automatically unfurling the bag comprises a shape memory effect metal insert mounted in the surgical bag; and,
means for automatically opening the open end of the bag wherein the means for opening the open end of the bag comprises a shape memory effect metal loop mounted to the open end of the bag.

38. The surgical pouch of claim 37 wherein the shape memory effect metal comprises Nitinol.

39. A method of performing an endoscopic surgical procedure comprising;
inserting a trocar cannula into a body cavity of a patient;
inserting a surgical pouch device into the body cavity through the trocar cannula, the surgical pouch device comprising a cannula and a surgical pouch mounted thereto, said pouch having an open end and also having automatic unfurling means and automatic opening means for opening the open end, wherein the pouch is furled about the cannula; and,
automatically unfurling the surgical pouch and opening the open end in the body cavity.

* * * * *